(12) United States Patent
Schanze et al.

(10) Patent No.: US 9,125,415 B2
(45) Date of Patent: Sep. 8, 2015

(54) THIOPHENE BASED OLIGOMERS AS LIGHT ACTIVATED BIOCIDES

(75) Inventors: Kirk S. Schanze, Gainesville, FL (US); Anand Parthasarathy, Naperville, FL (US); Subhadip Goswami, Gainsville, FL (US); David G. Whitten, Albuquerque, NM (US); Eunkyung Ji, Ervy le Chatel (FR); Thomas S. Corbitt, Albuquerque, NM (US); Dimitri Dascier, Ervy le Chatel (FR)

(73) Assignees: STC, UNM, Albuquerque, NM (US); University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 14/127,465

(22) PCT Filed: Jul. 5, 2012

(86) PCT No.: PCT/US2012/045598
§ 371 (c)(1),
(2), (4) Date: May 7, 2014

(87) PCT Pub. No.: WO2013/055417
PCT Pub. Date: Apr. 18, 2013

(65) Prior Publication Data
US 2014/0341776 A1 Nov. 20, 2014

Related U.S. Application Data

(60) Provisional application No. 61/505,590, filed on Jul. 8, 2011.

(51) Int. Cl.
| | | |
|---|---|---|
| A01N 43/82 | (2006.01) | |
| A01N 43/10 | (2006.01) | |
| C07D 409/14 | (2006.01) | |
| C07D 417/14 | (2006.01) | |
| A01N 43/647 | (2006.01) | |
| A61L 2/08 | (2006.01) | |
| A61L 2/16 | (2006.01) | |

(52) U.S. Cl.
CPC ............ *A01N 43/82* (2013.01); *A01N 43/10* (2013.01); *A01N 43/647* (2013.01); *A61L 2/084* (2013.01); *A61L 2/16* (2013.01); *C07D 409/14* (2013.01); *C07D 417/14* (2013.01)

(58) Field of Classification Search
CPC .......... A61L 2/16; A61L 2/084; A01N 43/82; A01N 43/647; A01N 43/10
USPC ............. 422/22; 514/362, 444, 359; 548/126, 548/260; 549/59
See application file for complete search history.

(56) References Cited

U.S. PATENT DOCUMENTS

| | | |
|---|---|---|
| 6,841,669 B2 | 1/2005 | Cipriani et al. |
| 2010/0035948 A1 | 2/2010 | Kumar et al. |

FOREIGN PATENT DOCUMENTS

| | | |
|---|---|---|
| WO | WO-2010044743 A1 | 4/2010 |
| WO | WO-2013055417 A2 | 4/2013 |
| WO | WO-2013055417 A3 | 4/2013 |

OTHER PUBLICATIONS

International Application Serial No. PCT/US2012/045598, International Search Report mailed May 27, 2013, 3 pgs.

International Application Serial No. PCT/US2012/045598, Written Opinion mailed May 27, 2013, 4 pgs.

Isabel, Ferreira C.F.R, et al., "Screening of antimicrobial activity of diarylamines in the 2,3,5-trimethylbenzo[b]thiophene series a structure-activity evaluation study", Bioorganic & Medicinal Chemistry Letters 14, (2004), 5831-5833.

Yanli, Tang, et al., "Light-induced antibacterial activity of symmetrical and asymmetrical oligophenylene ethynylenes", Langmuir 2011, (Mar. 15, 2011), 4956-4962.

"International Application Serial No. PCT/US2012/045598, International Preliminary Report on Patentability mailed Jan. 23, 2014", 6 pgs.

Arnt, Lachelle, et al., "Cationic Facially Amphiphilic Poly(phenylene ethynylene)s Studied at the Air-Water Interface", *Langmuir*, 19(61, (2004), 2404-2408.

Arnt, Lachelle, et al., "New Poly(phenyleneethynylene)s with Cationic, Facially Amphiphilic Structures", *Journal of the American Chemical Society*,124(26), (2002), 7664-7665.

Arnt, Lachelle, et al., "Nonhemolytic Abiogenic Polymers as Antimicrobial Peptide Mimics", *J. Polym. Sci Part A: Polym. Chem.* 42(15), (2004), 3860-3864.

Beaujuge, Pierre M., et al., "Spectral Engineering in pie-Conjugated Polymers with Intramolecular Donor-Acceptor Interactions", *Accounts of Chemical Research*, 43(11), (Nov. 2010), 1396-1407.

Fang, Zhen, et al., "Low-Bandgap Donor-Acceptor Conjugated Polymer Sensitizers for Dye-Sensitized Solar Cells", *Journal of the American Chemical Society*, 133(9), (2011), 3063-3069.

(Continued)

*Primary Examiner* — Sean E Conley
(74) *Attorney, Agent, or Firm* — Schwegman Lundberg & Woessner, P.A.

(57) ABSTRACT

Thiophene containing water-soluble oligomers were synthesized and characterized. The photophysical properties of these compounds were studied; transient absorption spectroscopy was used to probe the triplet excited state and their ability to sensitize singlet oxygen was spectroscopically monitored in deuterated methanol. The above compounds were tested for their light activated biocidal properties against *S. aureus* both under UV and visible radiation. Among the oligomers studied, the terthiophene derivative was found to kill the bacteria efficiently.

20 Claims, 8 Drawing Sheets

(56) References Cited

OTHER PUBLICATIONS

Ista, Linnea K., et al., "Conjugated-Polyelectrolyte-Grafted Cotton Fibers Act as "Micro Flypaper" for the Removal and Destruction of Bacteria", *ACS Applied Materials & Interfaces*, 3(8), (2011), 2932-2937.

Ji, Eunkyung, et al., "Antibacterial Activity of Conjugated Polyelectrolytes with Variable Chain Lengths", *Langmuir*, 27, (2011), 10763-10769.

Ji, Eunkyung, et al., "Light and Dark-Activated Biocidal Activity of Conjugated Polyelectrolytes", *ACS Applied Materials & Interfaces*, 3(8), (2011), 2820-2829.

Jiang, Hui, et al., "Conjugated Polyelectrolytes: Synthesis, Photophysics, and Applications", *Angew. Chem. Int. Ed.*, 48(24), (2009), 4300-4316.

Kenawy, El-Refaie, et al., "The Chemistry and Applications of Antimicrobial Polymers: A State-of-the-Art Review", *Biomacromolecules*, 8(2, (2007), 1359-1384.

Patel, Dinesh G., et al., "It Takes More Than an Imine: The Role of the Central Atom on the Electron-Accepting Abilitty of Benzotriazole and Benzothiadiazole Oligomers", *Journal of the American Chemical Society*, 134(5), (2012), 2599-2612.

Tang, Yanli, et al., "Synthesis, Self-Assembly, and Photophysical Properties of Cationic Oligo(p-phenyleneethynylene)s", *Langmuir*, 27(8), (2011), 4945-4955.

Wang, Yingsheng, et al., "Photochemical probes of intramolecular electronc and energy transfer", *Chemical Physics*, 176, (1993), 305-319.

Zhou, Zhijun, et al., ""End-Only" Functionalized Oligo(phenylene ethynylene)s: Synthesis, Photophysical and Biocidal Activity, *Journal of Physical Chemistry Letters*, 1 (21), 3207-3212.

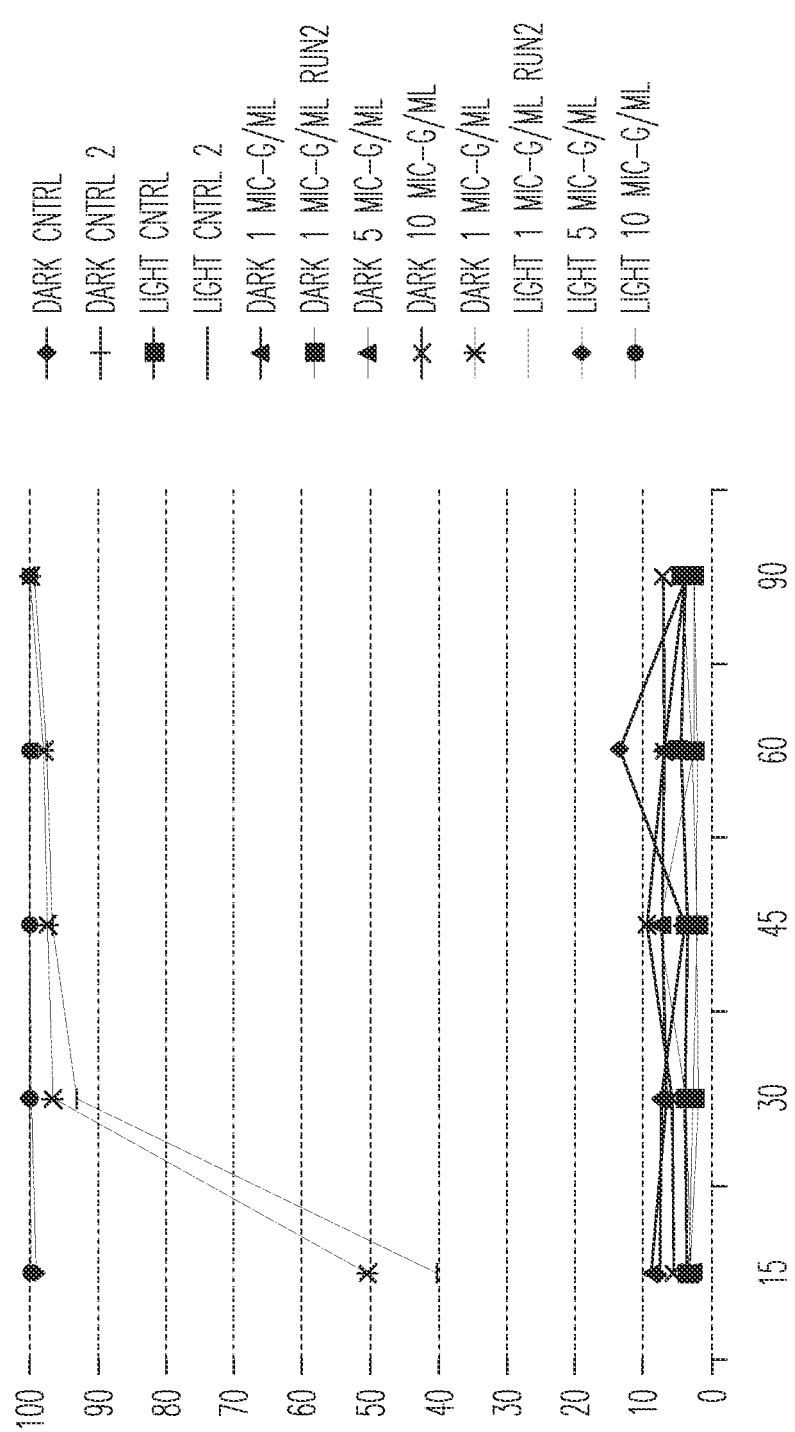

THIOPHENE BASED OLIGOMERS AS LIGHT ACTIVATED BIOCIDES

CROSS-REFERENCE TO RELATED APPLICATION

This application is a U.S. National Stage Application under 35 U.S.C. 371 from International Application No. PCT/US2012/045598, filed Jul. 5, 2012 which claims the benefit of priority of U.S. Provisional Patent Application No. 61/505,590, filed Jul. 8, 2011, both of which are incorporated by reference herein in their entirety.

STATEMENT OF GOVERNMENT SUPPORT

This invention was made with government support under T-TDTRA 1-07-0036, awarded by the Defense Threat Reduction Agency. The U.S. government has certain rights in the invention.

BACKGROUND

Controlling bacterial infections is of immense importance with applications ranging from health care setting to improving the quality of day to day life.[1] The increase of bacterial resistance to available antibiotics emphasizes the need for robust and versatile antimicrobials in controlling pathogenic bacteria. Different strategies have been developed towards new antimicrobial agents and polymers have taken the central stage as they have the advantage of being fabricated on to variety of formats.[2-5] We and others have explored and established the biocidal properties of cationic conjugated polyelectrolytes (CPEs).[2,6-8] Recently, we synthesized a series of cationic phenylene ethynylene oligomers (OPEs) with different lengths (repeat unit=1, 2, and 3) and examined structure-reactivity relationships between their photophysical photophysical properties and antibacterial activity.[9-12] These studies show that OPEs possess profound light activated biocidal activity. Photophysical studies reveal the OPEs are efficient sensitizers for singlet oxygen which is believed to play an important role in the light induced biocidal activity. The absorption of the OPEs is limited to the near-UV region, extending towards the violet region of the visible spectrum as the number of repeat unit increases to 3.

SUMMARY

In an effort to develop light activated oligomers that have strong absorption in the visible region, for improving the biocidal effectiveness of the compounds under visible, e.g., daylight, illumination, we turned our attention to thiophene based oligomeric compounds, such as oligomers featuring a donor-acceptor-donor (D-A-D) motif for the three aromatic rings. Here we disclose the synthesis, photophysical properties and light-activated biocidal activity of a set of three cationic, water-soluble, thiophene containing oligomers that feature varying donor-acceptor interactions. The absorption of these oligomers in the visible region increases with the strength of the acceptor unit. The results show that the biocidal activity of the oligomers can correlate with their photophysical properties.

The present invention is directed to cationic, water-soluble, thiophene containing oligomers, including a compound of formula (I)

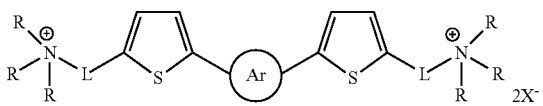

wherein
Ar is an aryl or heteroaryl ring system;
L is a linker comprising a 1-6 carbon chain, optionally comprising 1-2 heteroatom selected from the group consisting of O, NR, or $S(O)_q$ wherein q is 0, 1, or 2.
each R is independently alkyl or cycloalkyl, or 2 R together with the nitrogen atom to which they are bonded form a heterocyclyl, or 3 R together with the nitrogen atom to which they are bonded form a bicycloheterocyclyl; and,
each X is independently an anion.
Accordingly, in various embodiments, the invention provides a compound of any of the following formulas 4a, 4b, or 4c:

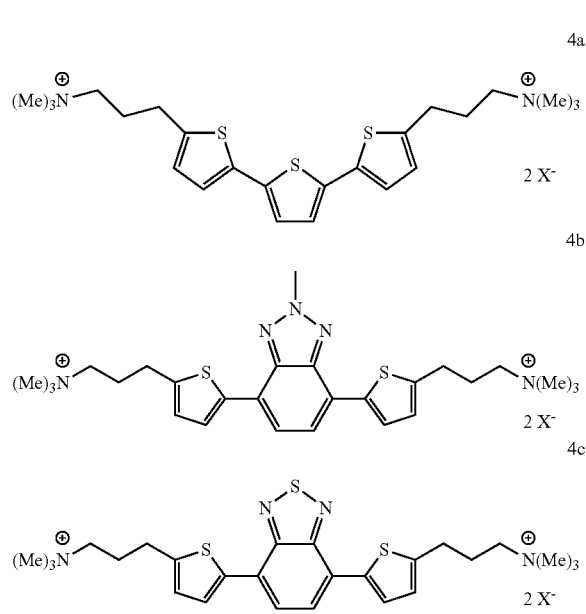

wherein X is a counterion, such as chloride, for the cationic organic component. In many embodiments, such biocidal compounds are water-soluble due to their ionic nature.

In various embodiments, the invention provides a method of killing a microorganism or attenuating a population of the microorganism, comprising contacting the microorganism or the population thereof with an effective amount or concentration of a compound of the invention, optionally under illumination, such as with visible or UV light, such as in atmospheric air or other conditions where oxygen is present.

For example, the invention can provide a method of decontaminating a surface contaminated with a microorganism or a population thereof, comprising contacting the microorganism or the population thereof disposed on the contaminated surface with an effective amount or concentration of a compound of the invention, optionally under illumination.

For example, the invention can provide a method of decontaminating a fabric contaminated with a microorganism or a population thereof, comprising contacting the microorganism or the population thereof disposed on or within fibers of the contaminated fabric with an effective amount or concentration of a compound of the invention, optionally under illumination.

For example, the invention can provide a method of decontaminating a transparent liquid contaminated with a microorganism or a population thereof, comprising contacting the microorganism or the population thereof disposed within the transparent liquid with an effective amount or concentration of a compound of the invention, optionally under illumination. For expression of the illumination-enhanced biocidal activity of the compound, the microorganism in contact with the biocidal compound can be exposed to levels of illumination sufficient to induce formation of toxic levels of singlet oxygen in the vicinity of the microorganism.

For example, the invention can provide a kit for decontamination of a surface, a fabric, or a transparent liquid, comprising a composition including the compound of the invention, optionally in a suitable solvent or medium; and, optionally, a source of illumination; optionally comprising additional biocidal materials; and optionally including instructions for use.

BRIEF DESCRIPTION OF THE FIGURES

FIG. 8 shows a time course of population kill of S. aureus in the presence of dark control, light control, indicated concentrations of compound 4a in the dark, and indicated concentrations of compound 4a under illumination.

DETAILED DESCRIPTION

Figure 1A:
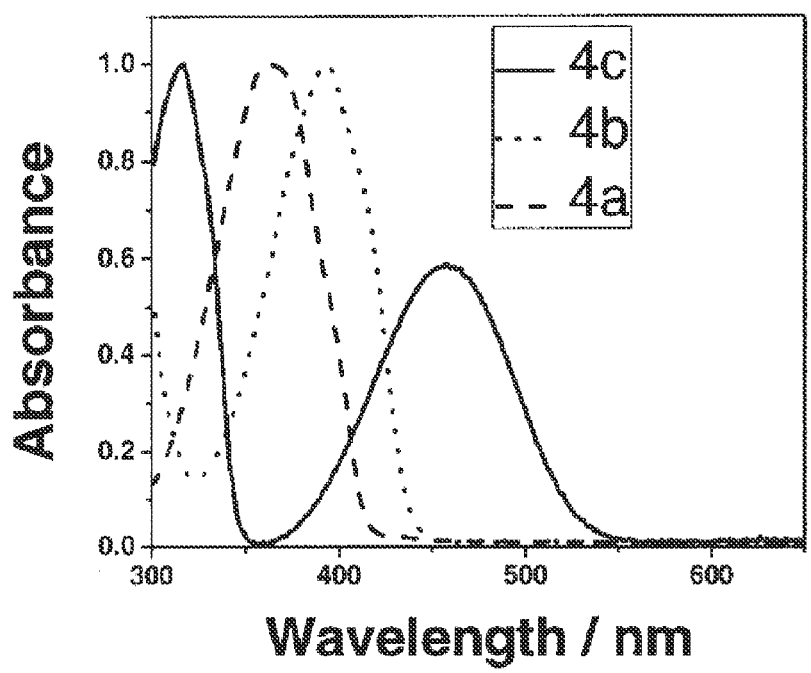
FIG. 1 shows (a) absorption, and (b) fluorescence spectra of the oligomers 4a-c in methanol.

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

Aspects of the present disclosure employ, unless otherwise indicated, techniques of chemistry, and the like, which are within the skill of the art. Such techniques are explained fully in the literature. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

The expression "effective amount", as used herein, refers to the amount of a compound of the invention that is effective to inhibit growth, kill, or otherwise negatively act on microorganisms such as pathogenic bacteria, wherein such inhibition, biocidal activity, or other action occurs to an extent sufficient to produce a beneficial decontaminating effect.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-buty I, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups, such as, but not limited to, bicycloalkyl groups like norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be monosubstituted or substituted more than once, such as, but not limited to, 2-, 3-, 4-, 5-, or 6-substituted phenyl or 2-8 substituted naphthyl groups, which can be substituted with carbon or non-carbon groups such as those listed above. Aryl groups can also bear fused rings, such as fused cycloalkyl rings, within the meaning herein. For example, a tetrahydronaphthyl ring is an example of an aryl group within the meaning herein. Accordingly, an aryl ring includes, for example, a partially hydrogenated system, which can be unsubstituted or substituted, and includes one or more aryl rings substituted with groups such as alkyl, alkoxyl, cycloalkyl, cycloalkoxyl, cycloalkylalkyl, cycloalkoxyalkyl, and the like, and also fused with, e.g., a cycloalkyl ring.

Heterocyclyl groups or the term "heterocyclyl" includes aromatic and non-aromatic ring compounds containing three or more ring members, of which, one or more is a heteroatom such as, but not limited to, N, O, and S. The sulfur S can be in various oxidized forms, such as sulfoxide S(O) or sulfone $S(O)_2$. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. Heterocyclyl groups can be monocyclic, or polycyclic, such as bicyclic, tricyclic, or higher cyclic forms. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, thiadiazolyl, pyridinyl, pyrimidinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Recently, π-conjugated, donor-acceptor electronic systems have received much attention owing to their utility in opto electronic devices such as polymer and organic solar cells where visible light absorption is important. While low band gap oligomers and polymers can be synthesized by this strategy, it also allows one to fine tune the band gap by varying the strength of the acceptor (refs).[13] Thiophene based donor-acceptor systems have gained popularity mainly due to their useful optical and electronic properties.[14-16]

According to various embodiments the present disclosure provides novel thiophene-based oligomers having light activated biocidal activity, methods for making them, and methods of using them as biocidal materials. According to an embodiment, thiophene-containing oligomers functionalized with cationic end groups were synthesized and tested for biocidal activity, and were found to be effective in killing the bacterial species *S. aureus*. The above-mentioned compounds absorb light in the near-UV region and emit in the visible region. Direct excitation with near-UV light (λ=355 nm) of these oligomers in both methanol and water solutions results in long lived transient absorption that extends throughout the visible region. The amplitude of transient absorption is relatively high in methanol in comparison to water indicating the higher triplet yield in the former solvent. These compounds were found to efficiently sensitize the formation of singlet oxygen in deuterated methanol. Our results indicate the terthiophene based oligomers kill *Staphylococcus aureus* under illumination, and can be effective biocidal agents for decontamination of media bearing populations of microorganisms, such as pathogenic bacteria.

The term "under illumination", as used herein, refers to illumination of a biocidal oligomer of the invention, such as in contact with a microorganism, or a surface contaminated with microorganisms, such as bacteria, with actinic radiation, i.e., visible or ultraviolet (UV) light. It is believed by the inventors herein that singlet oxygen generation in the presence of the inventive oligomers can be a mechanism in their biocidal activity. Accordingly, it is understood that such illumination can be carried out in the presence of oxygen, such as in atmospheric air, to provide the oxygen which is electronically excited into its singlet state. "Singlet oxygen", as is well known in the art, refers to the first electronic excited state of molecular oxygen $O_2$, which is a ground state triplet (i.e., two electrons with parallel spins), and can be excited into a singlet state (i.e., two electrons with antiparallel spins).

"Biocidal" activity, as the term is used herein, refers to action of the inventive compounds on living microorganisms whereby the compounds kill, block replication, control the population, or inhibit proliferation of the microorganisms, such as bacteria. It is believed that singlet oxygen can also be effective against other microorganisms, such as fungi, or against viral particles, or against bacterial or fungal spores. Biocidal activity can also occur versus eukaryotic organisms such as protozoans, and against multicellular organisms such as nematodes, insect larvae, the eggs of multicellular organisms, and the like. Due to the highly reactive nature of singlet oxygen, it is believed that a wide range of living or quasi-living (viral, spores, eggs, etc.) entities can be damaged or destroyed by use of compounds of formula (I) in the presence of illumination "Decontamination" of a material refers to the effect of biocidal activity on a population of target microorganisms or other living or quasi-living entities disposed on or within the material.

Thiophene containing oligomers were synthesized following the method outlined in Scheme S1, below. The synthesis requires 4 steps, with the key step involving a Stille coupling reaction. Final oligomers 4a, 4b, and 4c, were fully characterized, as discussed in the Examples. Comparison was made between the terthienyl 4a, wherein the central ring is a thienyl, compound 4b, wherein the central ring is a 1,2,3-benzotriazole, and compound 4c, wherein the central ring is a 2,1,3-benzothiadiazole.

The chemical structures of the thiophene based oligomers used in the study are shown above, wherein each "Me" signifies a methyl group. These oligomers were designed with several features in mind. First, each oligomer is "end-capped" with cationic —$(CH_2)_3N^+Me_3$ groups which renders the oligomers soluble in water and polar organic solvents. The oligomers exhibit strong biocidal activity that is believed to be due in part to their linear structure capped by cationic quaternary ammonium groups, which results in a strong propensity to bind and disrupt the bacterial membrane. Second, the π-conjugated structures of 4a-c feature a varying degree of D-A-D character which is expected to influence the HOMO-LUMO gap and visible light absorption properties. In particular, 4a features no D-A-D interaction, whereas 4b with central benzotriazole (BTz) and 4c with a benzothiadiazole (BTD) exhibit increased D-A-D character.

Figure 1B:
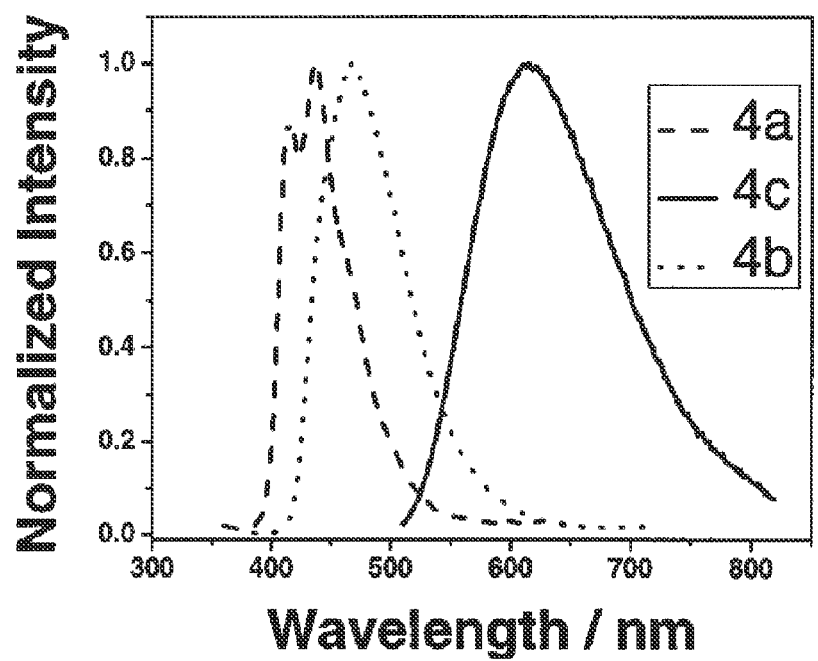
Figure 2A:
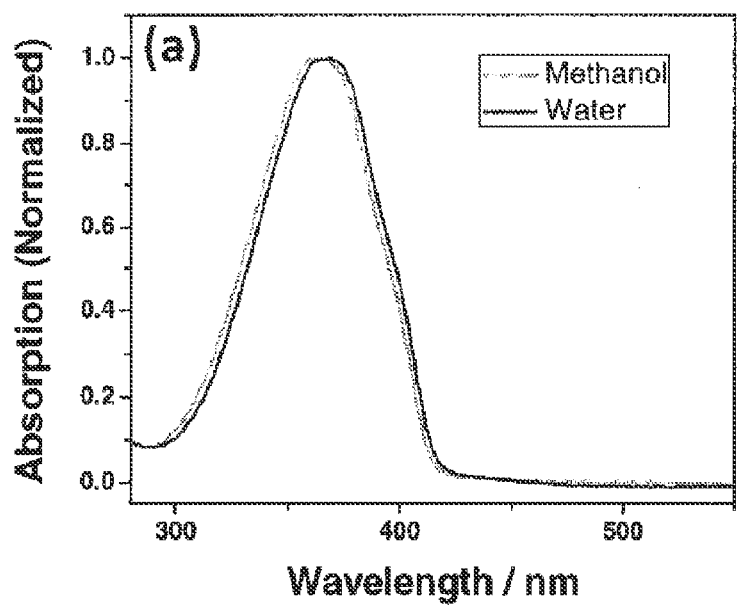
FIG. 2 shows absorption (a) and, emission (b) spectra of 4a in methanol and water.
Figure 2B:
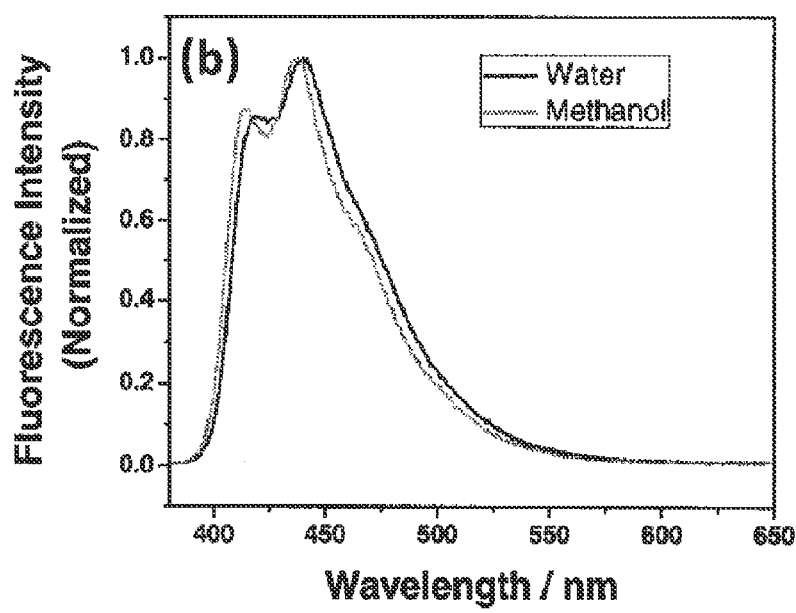
Figure 3A:
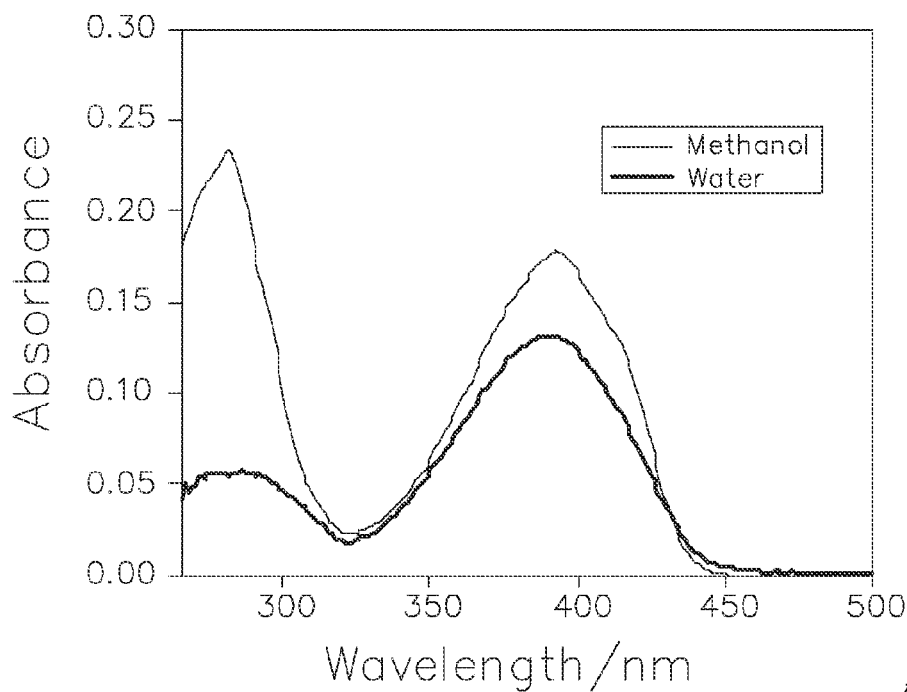
FIG. 3 shows absorption (a) and, emission (b) spectra of 4b in methanol and water.
Figure 3B:
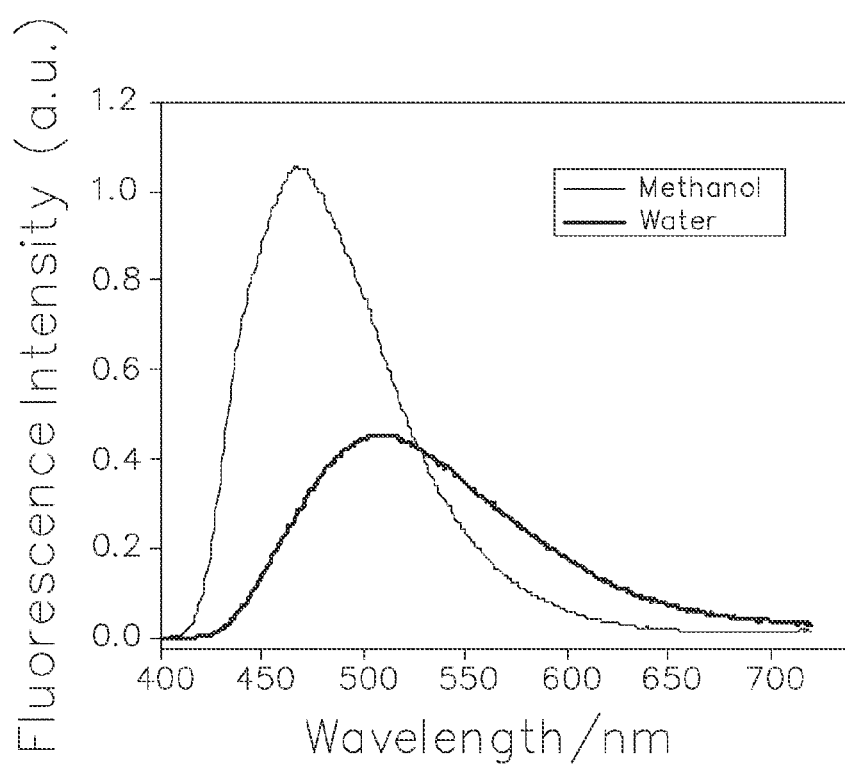
Figure 4A:
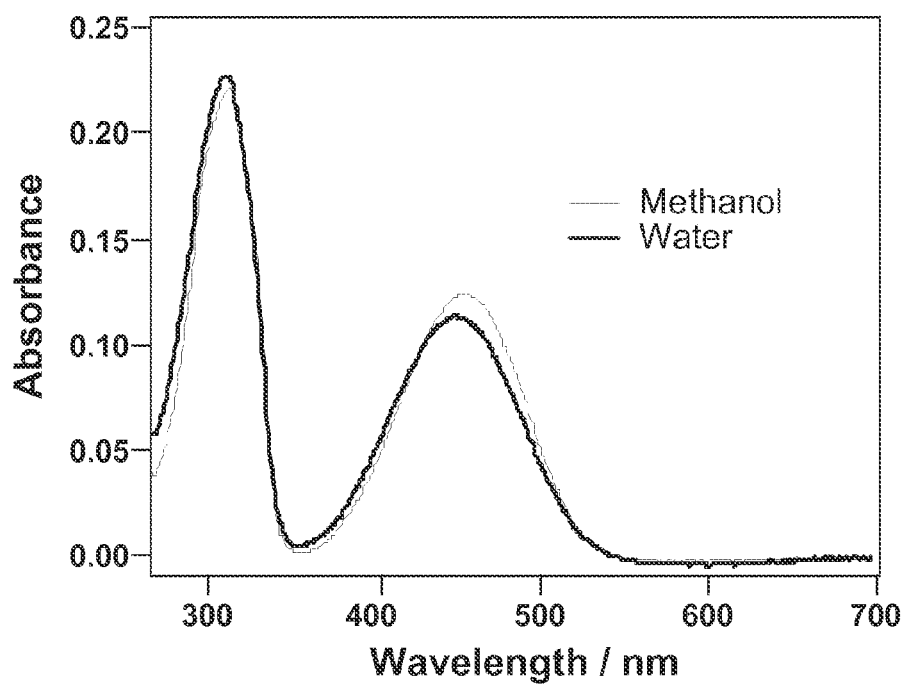
FIG. 4 shows absorption (a) and, emission (b) spectra of 4c in methanol and water.
Figure 4B:
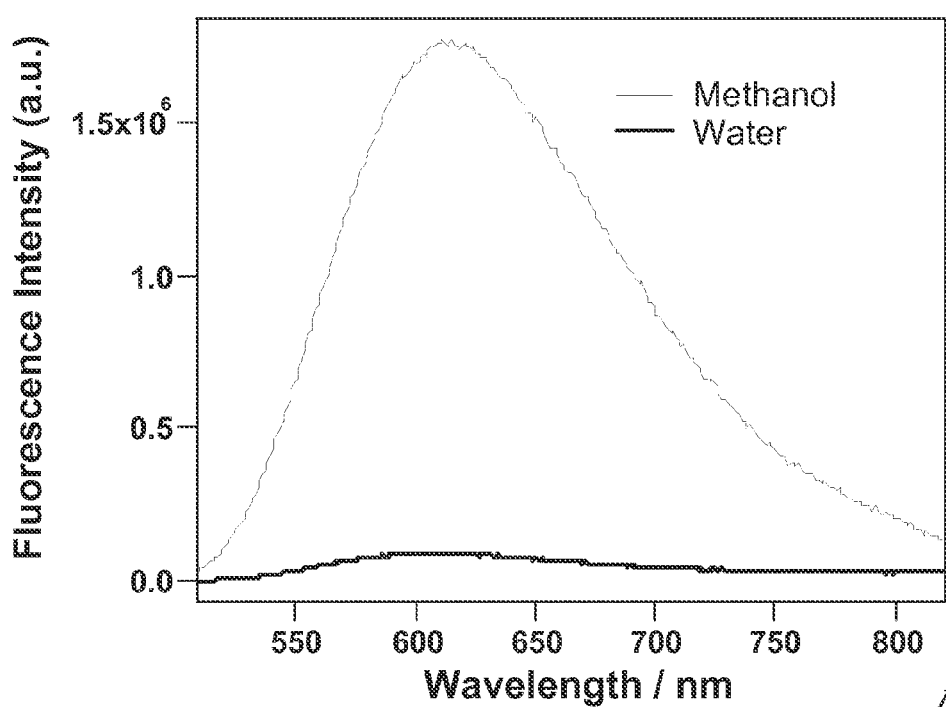

Oligomer 4a shows strong absorption in the near UV region characteristic of terthiophene (FIGS. 1, 2; and Tables 1, 2); the absorption of 4b is red shifted in comparison to 4a with the tail of absorption band extending well into the to the visible region (FIGS. 1, 3; and Tables 1, 2). This red shift induced by BTz is consistent with the studies by Patel et al., where they show that BTz functions as a weak electron acceptor in π-conjugated systems.[13] The absorption of 4c is further red shifted to ca. 457 nm (FIGS. 1, 4; and Tables 1, 2) due to intramolecular charge transfer consistent with the strong electron accepting nature of the BTD unit (ref). All the above oligomers show comparable UV absorption in methanol and water solution as well; the absorption is slightly red shifted for 4a (ca 4 nm) in water compared to methanol whereas a blue shift was observed for oligomers 4b and 4c (ca 3-5 nm) in water.

Oligomers 4a and 4b show blue fluorescence ($\lambda_{max}$=437 nm and 460 nm respectively, in methanol) whereas 4c exhibits a strong, red fluorescence ($\lambda_{max}$=615 nm). The fluorescence quantum yield of 4a is low and comparable both in methanol and water; however, the fluorescence quantum yield of 4b and 4c are much higher in methanol than in water. Close inspection of the fluorescence quantum yield data for 4a-c reveals an interesting correlation (Tables 1 and 2). For instance, the fluorescence quantum yield of oligomer 4a is lower than 4b and 4c in methanol. A similar trend is observed for the fluorescence lifetimes, i.e., the lifetime of the oligomer 4a was shorter than 4b and 4c.

Collectively, the these results clearly suggest that a rapid and efficient non-radiative decay pathway is active in 4a. In order to further understand this phenomenan, transient absorption spectroscopy was carried out to problem the triplet excited state.

TABLE 1

Photophysical data of substrates 4a-4c in methanol solution.

|  |  | 4a | 4b | 4c |
|---|---|---|---|---|
| $\lambda_{max}$ | MeOH | 364 | 390 | 457 |
| $\lambda_{max}$ | MeOH | 437 | 460 | 615 |
| $\Phi_F^a$ | MeOH | 0.06 ± 0.02 | 0.51 ± 0.02 | 0.23 ± 0.02[b] |
| $\Phi_\Delta^c$ | CD$_3$OD | 0.74 ± 0.02 | 0.49 ± 0.03 | d |
| $\tau_F$/ns (MeOH) |  | 0.18 (450 nm) | 2.2 (94%), 4.6 (6%) | 4.6 (85%) 8.2 (15%) |
| $TT_{Abs}$ (λ/nm)/ MeOH |  | 467 | 492 | 529 |
| $TT_{Abs}$ (ΔA, t=0) |  | 0.55 | 0.39 | 0.01 |
| $\tau_{triplet}$ (μs) |  | 2.7 | 2.1 | — |

[a]Measured using quinine sulfate in 0.1M sulfuric acid ($\Phi_F$ = 0.54) as actinometer.
[b]Fluorescein in 0.1M NaOH ($\Phi_F$ = 0.92) was used as actinometer.
[c]Measured in CD3OD using 2'-acetonaphthone ($\Phi\Delta$ = 0.79) as actinometer. [d] No detectable singlet oxygen was observed in CD$_3$OD.

Figure 5:
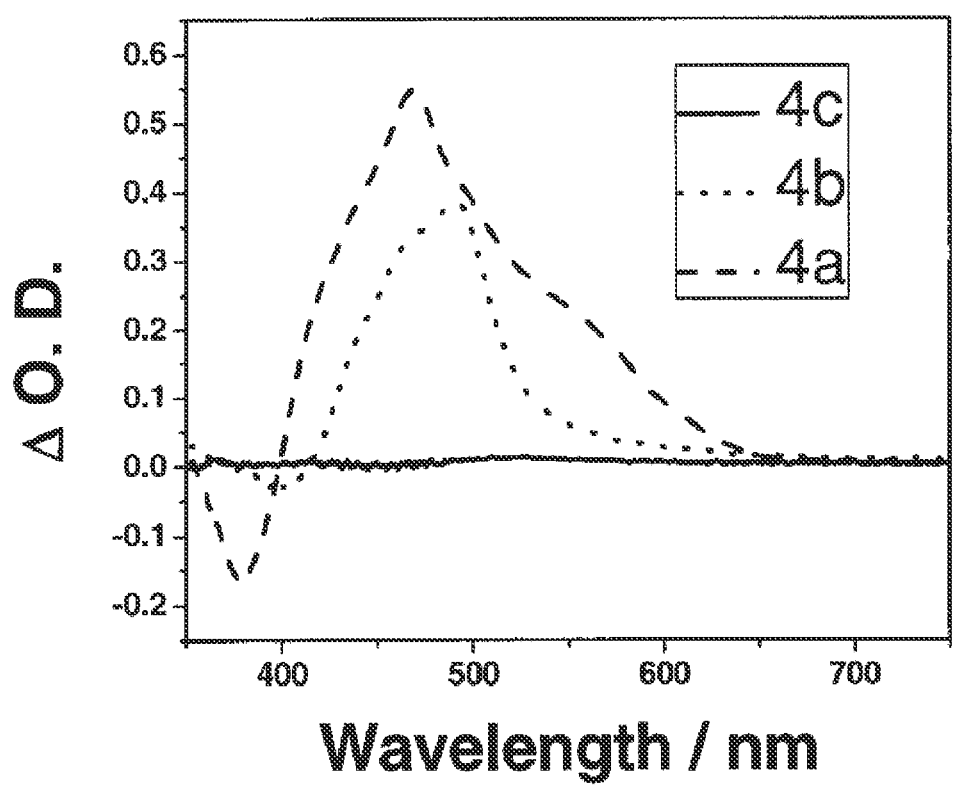
FIG. 5 shows transient absorption difference spectra of the oligomers (Abs=0.7 at $\lambda_{ex}$) immediately following the laser pulse ($TT_{Abs}$ ($\Delta A$, t=0)) in methanol ($\lambda_{ex}$=355 nm for 4a and 4b; 425 nm for 4c). Pulse energy and ground state absorption matched.
Figure 6A:
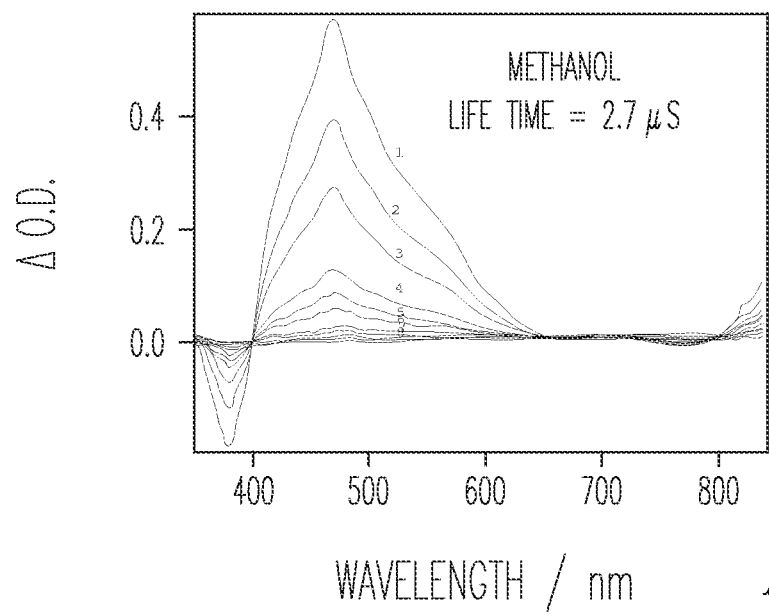
FIG. 6 shows transient absorption difference spectra of T3-NMe3 (compound 4a) chloride salt (laser energy 8 mJ, $\lambda$ex=355 nm) in (a) methanol (initial delay=50 ns, subsequent delay increments=1 µs), and (b) water (initial delay=50 ns, subsequent delay increments=17 µs). Spectral lines are numbered in sequence from the initial response through each subsequent delay increment. Samples were purged with argon for 45 min before the measurements. A higher life time is observed for the triplet excited state in water than in methanol.
Figure 6B:
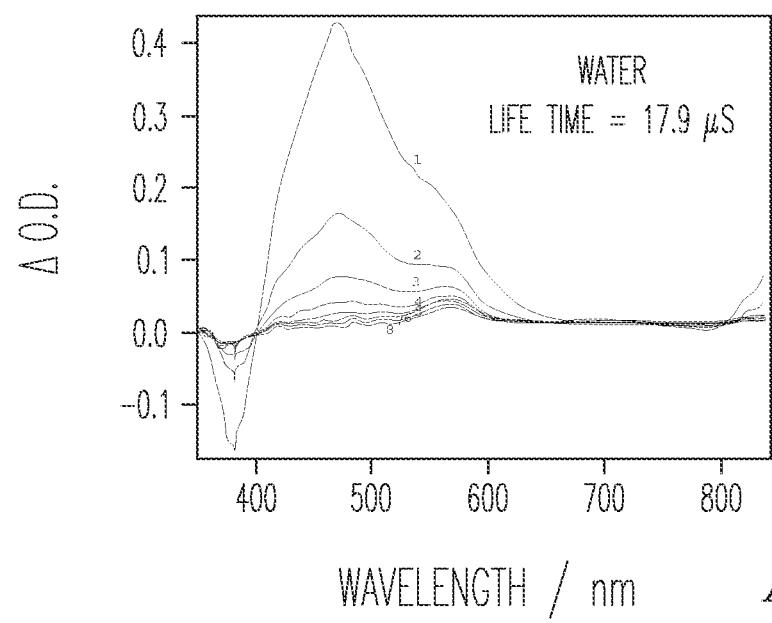

Transient absorption experiments were carried out both in methanol and in water (excitation at 355 nm, 5 ns pulse, 7 mJ·cm$^{-1}$ fluence). Since 4c does not absorb appreciably at 355 nm, the experiments were also carried out with excitation at 425 nm. The important photophysical data obtained in methanol solution are consolidated in Table 1 (see supporting information for data in aqueous solution). FIGS. 5 and 6 compare transient absorption difference spectra obtained immediately following the laser pulse in methanol. FIG. 5 shows transient absorption difference spectra of the oligomers (Abs=0.7 at $\lambda_{ex}$) immediately following the laser pulse ($TT_{Abs}$ (ΔA, t=0)) in methanol ($\lambda_{ex}$=355 nm for 4a and 4b; 425 nm for 4c). Pulse energy and ground state absorption matched. FIGS. 6A and 6B shows transient absorption difference spectra of T3-NMe$_3$ (compound 4a) chloride salt (laser energy 8 mJ, λex=355 nm) in (a) methanol (initial delay=50 ns, subsequent delay increments=1 μs), and (b) water (initial delay=50 ns, subsequent delay increments=17 μs), respectively. The response curves from each of the repetitive time increments is indicated by sequential numbers 1-8 in both FIGS. 6A and 6B. Samples were purged with argon for 45 min before the measurements. A higher life time is observed for the triplet excited state in water than in methanol.

TABLE 2

Photophysical data of substrates 4a-4c in water solution.

|  |  | 4a | 4b | 4c |
|---|---|---|---|---|
| $\lambda_{max}$ (Absorption/nm) | Water | 368 | 385 | 454 |
| $\lambda_{max}$ (Fluorescence/nm) | Water | 437 | 460 | 610 |
| $\Phi_F^a$ | Water | 0.058 ± 0.02 | 0.340 ± 0.02 | b |
| $\tau_{F/ns}$ (Water) |  | 0.19 (450 nm) | 3.4 (93%) 0.21 (7%) (500 nm) | 3.4 (95%) 0.3 (5%) (600 nm) |
| $TT_{Abs}$ (λ/nm) in Water |  | 467 | 492 | 529 |

TABLE 2-continued

Photophysical data of substrates 4a-4c in water solution.

|  | 4a | 4b | 4c |
|---|---|---|---|
| $TT_{Abs}$ (ΔA, t = 0) in Water | 0.43 | — | — |
| $\tau_{triplet}$ (μs) in Water | 17.9 | — | — |

[a] Measured using Quinine sulfate in 0.1M sulfuric acid ($\Phi_F$ = 0.54) as actinometer.
[b] The quantum yield data could not be obtained due to the compounds weak emission in water
[c] life time could not be obtained due to very low fluorescence.

Oligomers 4a and 4b exhibit strong transient absorption throughout the visible region; the transients decay with τ=1-3 μs in methanol and they are quenched in air saturated solution; those features are consistent with the assignment of the absorption to the triplet state. Interestingly, when transient absorption is carried out under the same excitation energy, 4c exhibits little or no transient absorption. Inspection of the initial amplitude of the TT absorption immediately following the laser pulse ($TT_{Abs}$ (ΔA, t=0), Table 1) gives useful information regarding the relative triplet yield. The data reveals that the TT absorption of 4a is substantially larger than for the other oligomers, suggesting a higher triplet yield. This correlates well with the other fluorescence data discussed above.

The important and necessary feature of the biocidal agents triggered by light is their ability to sensitize the formation of singlet oxygen. Having established the formation of triplet state by direct excitation of the oligomers 4a and 4b (but not 4c), we determined their ability to sensitize singlet oxygen in deuterated methanol ($\Phi_A$, Table 1). The oligomers 4a and 4b sensitize the formation of singlet oxygen very efficiently, as evidenced by the observation of emission at 1260 nm; notably, 4c does not produce much triplet and in consistent with this observation no singlet oxygen emission was detected for 4c. From the above results it is evident that the oligomer with terthiophene back bone is the most efficient sensitizer for singlet oxygen.

Figure 7:
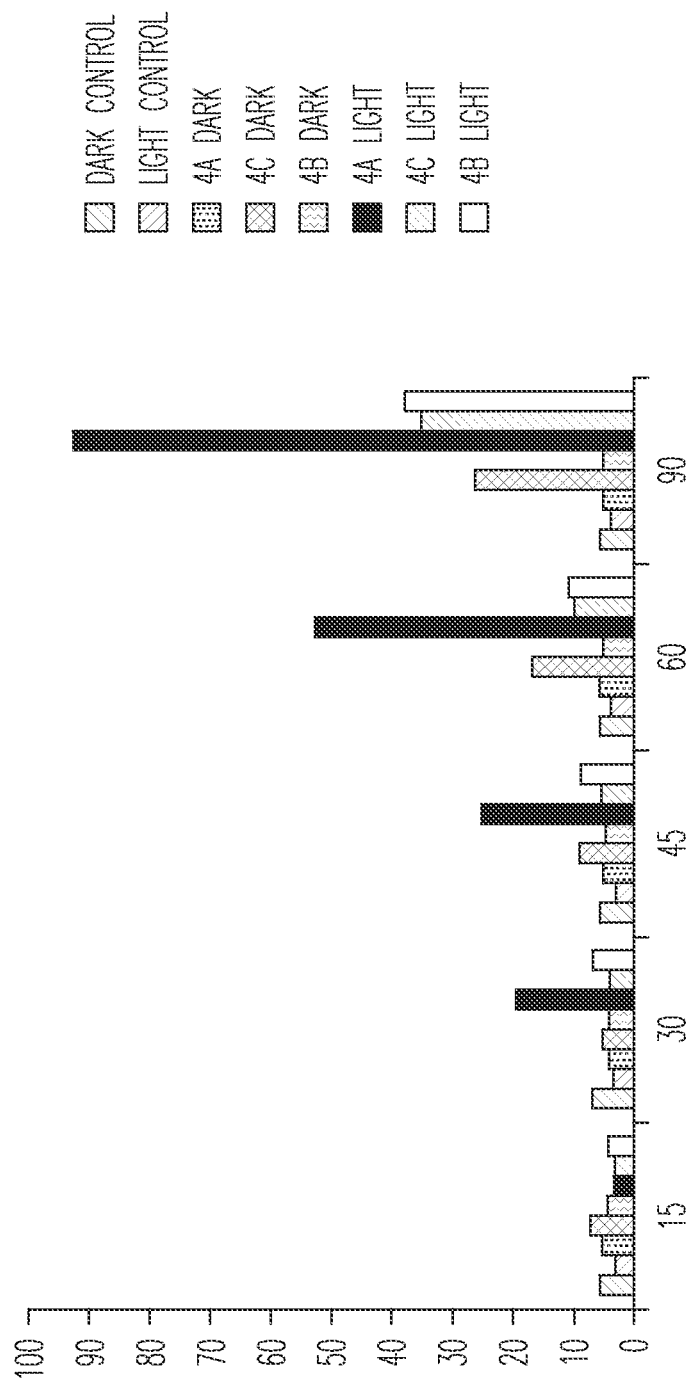
FIG. 7 shows the percentage of killed S. aureus cells in the presence of 1 µg/mL oligomer solutions following exposure to visible light and incubation in dark for 0, 15, 30, 45, 60, and 90 min.

There has been an increasing interest in the prevention of staphylococcal infections because of the increasing number of infections caused by methicillin-resistant *S. aureus* (MRSA), which is the most common cause of hospital-acquired infections. Our previous studies with oligo (phenylene ethynylene) type oligomers have clearly established that these oligomers are effective against variety of bacteria in the presence of light. Notably, all the studied oligomers sensitize singlet oxygen and kill bacteria efficiently upon excitation with UV light; moreover, singlet oxygen quantum yield of these oligomers showed a good correlation with the biocidal behavior. As our objective is to develop visible light activated biocidal oligomers, we investigated the antibacterial activity of compounds 4a-c and against *Staphylococcus aureus* (*S. aureus*). After oligomer solutions were incubated with *S. aureus* under visible light illumination or in the dark, the antibacterial effect of the three oligomers was evaluated at time 0, 15, 30, 45, 60, and 90 min by flow cytometry analysis after staining the bacterial suspensions with live/dead fluorescent dyes (SYTO21, green fluorescence=live, and propidium iodide, red fluorescence=dead). FIGS. 7 and 8 show plots of the percentage of dead bacteria cells versus light exposure time of the thiophene-based oligomeric series at 1/mL. These results are in close agreement with our predictions: 4a having the highest singlet oxygen quantum yield shows the best antibacterial activity against *S. aureus* under light exposure. As indicated in FIGS. 7 and 8, ~93% of bacteria were killed by 4a after 90 min of irradiation while 4b and 4c kills only about 35% of bacteria. The antibacterial efficiency of three oligomers increases with increasing irradiation time. In the control sample where oligomers were not added to the bacterial suspension most cells (>90% as shown in flow cytometry data) were viable and appear green fluorescence. Dark antibacterial activity was not observed from 4a and 4b; however, 4c kills ~27% of bacteria after 90 min of incubation of bacteria with 4c.

Based on the photophysical results and our previous studies with conjugated poly- and oligo-electrolytes, we believe the following steps are involved in the light activated biocidal action: (1) oligomers associate and penetrate onto the negatively charged bacterial membrane, (2) oligomers, upon exposure to visible light, sensitize singlet oxygen and/or reactive oxygen species at the interface between the oligomers and the bacteria surfaces or inside the bacterial membrane, and (3) singlet oxygen and/or reactive oxygen species trigger bacterial inactivation via oxidization of bacterial proteins or lipids.

Oligomers 4a-c retained the light activated antibacterial activity when the visible light was substituted with UV light. It once again became evident from the above results that 4a is the most efficient compound in killing bacteria in the presence of light. The efficiency of the oligomers under visible light excitation are in the same order as UV excitation, i.e., 4a>4b~4-c. The above results show considerable correlation with the photophysical results obtained. Consistent with its ability to sensitize singlet oxygen ($\Phi_A$–0.74), the oligomer 4a is the most efficient light activated biocide of three oligomers studied. Albeit having a moderate efficiency for singlet oxygen generation ($\Phi_A$–0.49), the oligomer 4b is not as efficient in achieving bacterial kill as 4a and 4c are.

This result shows that not only the electrostatic interaction between the sensitizer and bacterial membrane but also other factors like hydrophobic effect and shape of the sensitizer are also important in determining the proximity and interaction between the bacterial membrane and sensitizer; this is vital as the produced singlet oxygen has a very short life time in water. In spite of no observable singlet oxygen senitization in $CD_3OD$, 4c shows light activated killing which is comparable to 4b; this is surprising result can be attributed to the stronger absorption of 4c coupled with its ability to interact and destroy the bacterial membrane as evidenced by its dark biocidal activity (27% of bacteria after 90 min of incubation).

We have developed a synthetic strategy to make water-soluble, thiophene based oligomers. Introduction of BTD, a strong acceptor, shifts absorption to visible region but diminishes the compound's ability to sensitize singlet oxygen. On the other hand, the terthiophene based oligomer is a very efficient singlet oxygen sensitizer and results in bacterial kill when exposed to visible light. Overall, our results clearly signify the importance of other factors like the structure of the backbone and polarity which would in turn influence the interaction between the sensitizer and bacterial membrane. This is important as the generated singlet oxygen has a very short life time in the aqueous medium. We believe our studies would be of significant importance and aid in the development of new donor-acceptor type molecules for controlling pathogenic bacteria and other noxious organisms. Using criteria we have identified, e.g., that a higher absorptivity of light of a particular wavelength, i.e., a higher extinction coefficient for the compound at the wavelength, correlates with a higher degree of biocidal activity under illumination by light of that wavelengths at equimolar concentrations. Accordingly, biocidal compounds of formula (I) can be identified as being of enhanced biocidal activity for certain types of illumination, e.g., daylight illumination, UV illumination, and the like, based upon their extinction coefficients at the illuminating wavelengths. The extinction coefficient can be altered by selection of the appropriate aryl or heteroaryl moiety Ar in formula (I), so that compounds of particular effectiveness can be designed for conditions where illumination of the target organisms under particular lighting conditions will take place. Accordingly, the invention can provide a method of designing a phototoxic oligomer of formula (I) for use under conditions of illumination by light of wavelength λ, the method comprising selecting an Ar group with electron donor or acceptor properties suitable to provide the oligomer of formula (I) incorporating the Ar group with a high extinction coefficient for absorption of light at wavelength λ.

Synthesis of Compositions of the Invention

Compounds of the invention can be prepared according to the above Scheme S1, in conjunction with ordinary skill in organic synthesis. Specific procedures are provided below in the Examples section.

Oligomer 4a, 4b, and 4c Structures

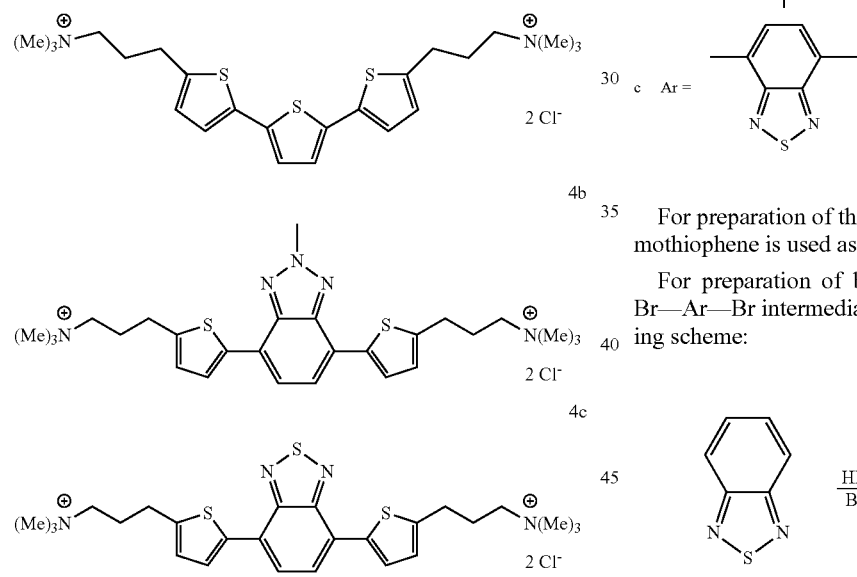

Scheme S1: Synthesis of thiophene based oligomers

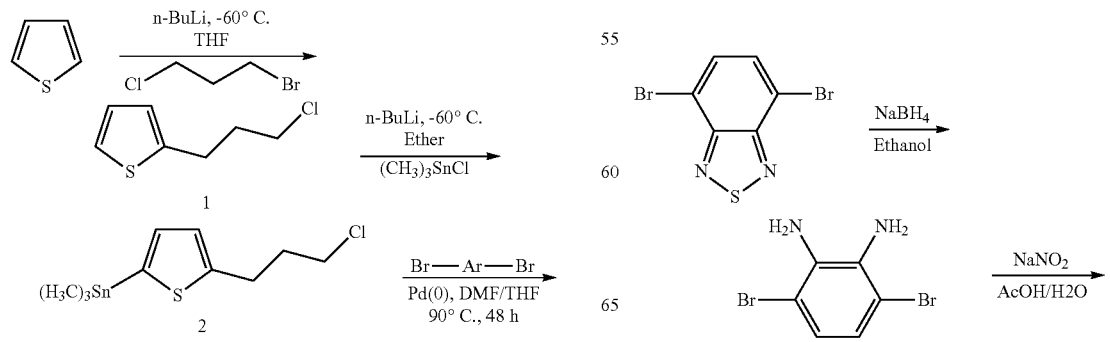

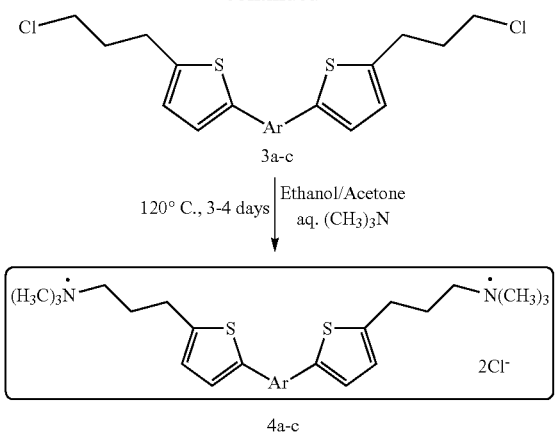

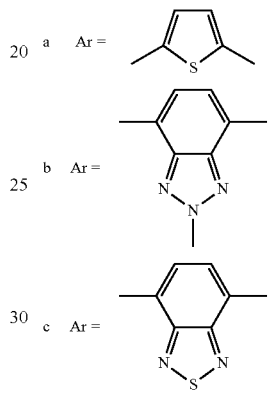

For preparation of the terthienyl compound 4a, 2,5-dibromothiophene is used as Br—Ar—Br in the above scheme.

For preparation of benzothiadiazolyl compound 4c the Br—Ar—Br intermediate can be prepared using the following scheme:

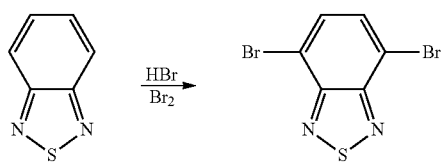

For preparation of the benzotriazolyl compound 4b, the Br—Ar—Br intermediate can be prepared using the following scheme:

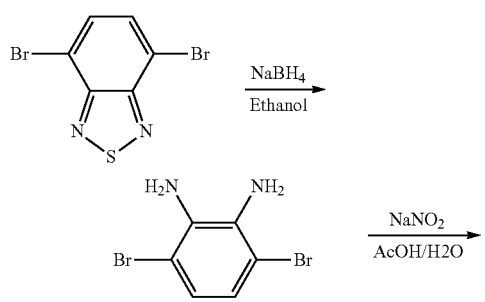

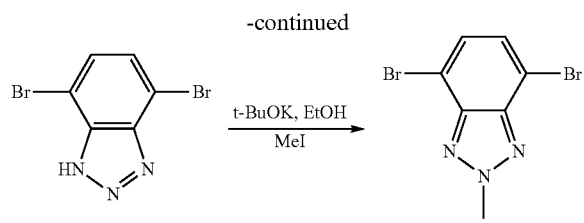

Other aryl and heteroaryl moieties can be incorporated into analogous structures using the same methods, but substituting the appropriate dibromoaryl intermediates.

Uses of Compositions of the Invention

In various embodiments, the invention provides a method of killing a microorganism or attenuating a population of the microorganism, comprising contacting the microorganism or the population thereof with an effective amount or concentration of a compound of the invention, optionally under illumination, such as with visible or UV light, such as in atmospheric air or other conditions where oxygen is present. As shown in the bioassay results, FIG. 7, showing in bar graph format the percentage of killed *S. aureus* cells in the presence of 1 µg/mL oligomer solutions, following exposure to visible light and incubation in dark for 0, 15, 30, 45, 60, and 90 min. All the compounds 4a, 4b, and 4c showed marked light-dependent toxicity versus the bacterial cells, while only compound 4c showed significant dark toxicity under the same conditions.

FIG. 8 shows quantitative data for compound 4a at various concentrations in the presence and absence of light with respect to biocidal activity over the indicated time in minutes versus *S. aureus*. The data show that in the presence of light, compound 4a is an effective biocide at concentrations down to 1 µg/mL within 30 minutes. At higher concentrations of 5 and 10 µg/mL, the compound virtually eliminates the bacterial population within a few minutes.

It is believed by the inventors that the oligomers of this structural class, in the presence of illumination, are effective against a wide variety of species of microorganisms, e.g., bacteria, fungi, protozoans, and the like. It can also be biocidal versus multicellular organisms such as insect larvae, nematodes, and the like. The mechanism by which such antimicrobial bioactivity takes place, believed to involve the generation of singlet oxygen in situ, in proximity to the target organisms, is believed to be of a general nature, in that bacterial membranes across a wide variety of species, as well as cell membranes of fungi, protozoans, algae, and even multicellular organisms, can be susceptible to the degradative effects of the highly reactive singlet oxygen. Likewise, it is believed by the inventors herein that it is unlikely that resistance can readily develop, due to the non-selective disruption of membrane functions based on membrane components present in virtually all living organisms. Contacting the target organisms with an effective amount or concentration of a biocidal oligomer of the invention, in the presence of sufficient light to generate singlet oxygen, can result in cell membrane disruption and death.

For example, the invention can provide a method of decontaminating a surface contaminated with a microorganism or a population thereof, comprising contacting the microorganism or the population thereof disposed on the contaminated surface with an effective amount or concentration of a compound of the invention, optionally under illumination. As described above, a population of microorganisms, such as pathogenic bacteria, disposed on a surface, such as the surface of a surgical instrument or facility, or a sterile surface in a processing facility, can be decontaminated by exposing the population to light in the presence of an effective level of a biocidal oligomer of the invention. The surface can be virtually any material, such as metal, glass, ceramic, plastic, or the like, provided that the surface can be illuminated.

For example, the invention can provide a method of decontaminating a fabric contaminated with a microorganism or a population thereof, comprising contacting the microorganism or the population thereof disposed on or within fibers of the contaminated fabric with an effective amount or concentration of a compound of the invention, optionally under illumination. A fabric, consisting of fibers, can harbor populations of pathogenic bacteria disposed on and within the fibers. Exposure of the bacteria, such as by soaking the fabric in a water or alcohol solution of a biocidal oligomer of the invention, concurrently with or prior to exposure to visible or UV light, can be used to effectively decontaminate the fabric. Fabrics such as bed sheets, bandages, clothing, and the like can be decontaminated using the biocidal oligomers of the invention in conjunction with illumination.

For example, the invention can provide a method of decontaminating a transparent liquid contaminated with a microorganism or a population thereof, comprising contacting the microorganism or the population thereof disposed within the transparent liquid with an effective amount or concentration of a compound of the invention, optionally under illumination. For expression of the illumination-enhanced biocidal activity of the compound, the microorganism in contact with the biocidal compound can be exposed to levels of illumination sufficient to induce formation of toxic levels of singlet oxygen in the vicinity of the microorganism. Compositions of the invention can thus be used to kill bacterial populations in, for example, water that is to be used for washing purposes. If it is desired to subsequently remove the biocidal compounds from the water, the ionic nature of the compounds can be used to remove them from the water using an ion-exchange resin or the like.

For example, the invention can provide a kit for decontamination of a surface, a fabric, or a transparent liquid, comprising a composition including the compound of the invention, optionally in a suitable solvent or medium; and, optionally, a source of illumination; optionally comprising additional biocidal materials; and optionally including instructions for use. For decontamination of objects or materials, capable of being exposed to illumination, a kit can be provided including a biocidal oligomer of the invention, such as in water or alcohol solution, in conjunction with instructions for use. A light source (visible or UV) can also be included in the kit; alternatively, sunlight or artificial illumination can be used as a light source. The solution containing the biocidal oligomer can further contain other sterilizing ingredients, such as surfactants, provided they do not react with the inventive oligomer. The chemical stability of the inventive oligomers, which is believed to be of a high degree due to the robust chemical structures, can make them compatible with a wide range of other sterilant materials. Or, the kit can include a second container with a sterilant, such as an oxidizing agent, a halogen, or the like, for separate application to the object or material to be sterilized.

EXAMPLES

Instrumentation and Methods.

NMR spectra were recorded using a Varian VXR-300 FT-NMR, operating at 300 MHz for $^1$H NMR and at 75.4 MHz for $^{13}$C NMR. UV-Visible spectra were recorded using a Varian Cary 100 dual beam spectrophotometer. Corrected steady-state fluorescence spectra were obtained with a PTI spectrometer. A 1 cm square quartz cuvette was used for solution spectra, and emission was collected at 90° relative to excitation beam. Fluorescence quantum yields are reported relative to known standards. The optical density of solutions at the excitation wavelength was ≤0.1, and corrections were applied for differences in the refractive index of standard and sample solutions. Transient absorption spectra were collected using a laser systems that is described elsewhere.[17,18] The optical density of the solutions was adjusted to ~0.7 at the excitation wavelength (355 nm) with the laser energy set at 6-7 mJ. Solutions were purged with argon for 45 min before making transient absorption spectroscopy measurements. Singlet oxygen quantum yields were measured using a Photon Technology International Quantamaster near-IR spectrophotometer equipped with an InGaAs photodiode detector, optical chopper and a lock in amplifier.

Synthesis of 2

A solution of 1 (1 g, 6.2 mmol, literature procedure) in anhydrous ether (5 ml) was cooled down to −50° C. under the protection of argon. 2.5 ml of 2.5 M BuLi in hexane (6.25 mmol) was added to it and the solution was allowed to warm up to 0° C. The solution was cooled back to −50° C. and 1.49 g (7.4 mmol) of $(CH_3)_3SnCl$ in about 3 ml ether was added to it drop wise through an addition funnel and the reaction was allowed to warm-up to room temperature and stirred overnight. The reaction mixture was washed with water, dried over sodium sulfate and solvent evaporated give an oil (2, yield ~90%) which was taken to the next step.

$^1H$ NMR ($CDCl_3$, δ ppm): 0.37 (s, 9H), 2.15 (m, 2H), 3.07 (t, 2H), 3.59 (t, 2H), 6.95 (d, 1H), 7.05 (d, 1H).

Synthesis of 3a

A solution of 2 (2 g, 6.2 mmol) and 2,5-dibromothiophene (0.57 g, 2.3 mmol) in 12 ml THF-DMF (1:1) mixture was purged with argon for 30 min. $Pd(PPh_3)_4$ (160 mg, 0.14 mmol) was added to the solution under the protection of argon and the reaction was heated to 90° C. for 24 h. After the reaction, solvent was evaporated under reduced pressure and the mixture was partitioned between water and chloroform. The chloroform layer was collected, dried over $Na_2SO_4$ and evaporated to give the crude product. The crude was further purified by column using 80:20 hexane-chloroform as eluent. The product was finally purified by precipitation over methanol and dried under vacuo (yield—260 mg, 28%). 3b and 3c were synthesized following the above experimental protocol.

3a: $^1H$ NMR ($CDCl_3$, δ ppm): 2.12 (m, 4H), 2.99 (t, 4H), 3.59 (t, 4H), 6.74 (d, 2H), 6.97 (d, 2H), 6.98 (s, 2H). $^{13}C$ NMR ($CDCl_3$, δ ppm): 27.27, 34.19, 43.98, 123.59, 123.96, 126.00, 135.51, 136.25, 142.84. APCI.MS $[M+H]^+$=401.0029 (Theoretical-401.0020).

3b: $^1H$ NMR ($CDCl_3$, δ ppm): 2.16 (m, 4H), 3.03 (t, 4H), 3.59 (t, 4H), 4.58 (s, 3H), 6.85 (d, 2H), 7.50 (s, 2H), 7.82 (d, 2H). $^{13}C$ NMR ($CDCl_3$, δ ppm): 27.40, 34.28, 43.86, 44.08, 122.76, 123.51, 126.42, 127.04, 138.22, 142.53, 144.03 APCI.MS $[M+H]^+$=450.0618 (Theoretical-450.0627).

3c: $^1H$ NMR ($CDCl_3$, δ ppm): 2.12 (m, 4H), 3.10 (t, 4H), 3.64 (t, 4H), 6.94 (d, 2H), 7.80 (s, 2H), 7.95 (d, 2H). $^{13}C$ NMR ($CDCl_3$, δ ppm): 27.40, 34.24, 44.05, 125.48, 125.96, 126.32, 127.67, 137.71, 145.27, 152.78. DART.MS $[M+H]^+$=453.0094 (Theoretical-453.0083).

Synthesis of 4 ($T_3$-$NMe_3$ Cl)

3 (40 mg, 0.1 mmol) was dissolved in mixture of 3 ml of ethanol and 2 ml acetone. 4 mL of 25% solution of trimethyl amine in water was added to it and the mixture was heated at 100° C. in a seal tube for 2-3 days. The solvent was then evaporated and the residue was taken up in methanol and precipitated over acetone (3 times). The yellow solid was filtered and dried under vacuo (yield—35 mg, 68%). 4b and 4c were synthesized following the above experimental protocol.

4a: $^1H$ NMR ($CD_3OD$, δ ppm): 2.19 (m, 4H), 2.95 (t, 4H), 3.15 (s, 18H), 3.40 (m, 4H), 6.87 (d, 2H), 7.04 (d, 2H), 7.06 (s, 2H). $^{13}C$ NMR ($CD_3OD$, δ ppm): 24.69, 26.27, 52.48, 65.83, 123.53, 123.88, 126.24, 135.56, 136.04, 142.04. ESI.MS $[M^{2+}]$=224.1025 (Theoretical-224.1015).

4b: NMR ($CD_3OD$, δ ppm): 2.19 (m, 4H), 2.99 (t, 4H), 3.12 (s, 18H), 3.39 (m, 4H), 4.57 (s, 3H), 6.98 (d, 2H), 7.58 (s, 2H), 7.93 (d, 2H). $^{13}C$ NMR ($CD_3OD$, δ ppm): 24.75, 26.39, 42.67, 52.47, 65.83, 122.16, 123.30, 126.33, 127.12, 138.26, 142.10, 143.08. ESI.MS $[M^{2+}]$=248.6325 (Theoretical-248.6318).

4c: NMR ($CD_3OD$, δ ppm): 2.23 (m, 4H), 3.01 (t, 4H), 3.13 (s, 18H), 3.41 (m, 4H), 7.00 (d, 2H), 7.90 (s, 2H), 8.00 (s, 2H). $^{13}C$ NMR ($CD_3OD$, δ ppm): 23.21, 24.85, 50.92, 64.30, 123.67, 124.12, 124.73, 126.12, 136.27, 142.87, 150.89. ESI.MS $[M^{2+}]$=250.1053 (Theoretical-250.1046).

Antibacterial Studies, Dead/Live Assays.

*Staphylococcus aureus* (ATCC 10832, American Type Culture Collection) was grown in Brain Heart Infusion (BHI, Difco) and stored at ~70° C. with 20% (v/v) glycerol (EMD) before use. Stock cultures maintained on agar plates (2%, Difco) were used to inoculate 50 mL cultures in liquid BHI. The cultures were incubated at 37° C. for 18 hours. The bacteria were then centrifuged and washed twice with 0.85% NaCl followed by counting in a hemocytometer to normalize bacterial concentration in 20 mL of 0.85% NaCl ($8\times10^6$ cells/mL) for antibacterial tests. Control samples containing only bacterial cells, and desired concentrations of oligomer/bacteria mixture samples were exposed to the visible light for 15, 30, 45, 60 and 90 min in a LuzChem ORG photoreactor using Sylvania T5 bulbs (λ=350-799 nm). Another set of samples were incubated in the dark for 15, 30, 45, 60 and 90 min. Then dead/live assays were conducted using SYTO21 (green fluorescence=live) and propidium iodide (red fluorescence=dead) purchased from Invitrogen. After bacteria were incubated with the oligomers in the light and dark conditions, a 1:1 ratio of dyes (2.4 μL) were added to the samples and kept in the dark for 15 min. Finally, the bacteria were examined using an Accuri C6 flow cytometer where $2\times10^4$ cells were analyzed from $8\times10^6$ cell solution. The number of live cells and dead cells corresponding to green and red fluorescence respectively were counted and compared by flow cytometry. Results are shown graphically in FIGS. 7 and 8.

DOCUMENTS CITED (1) Kenawy, E.-R.; Worley, S. D.; Broughton, R. *Biomacromolecules* 2007, 8, 1359-1384.
(2) Ji, E.; Corbitt, T. S.; Parthasarathy, A.; Schanze, K. S.; Whitten, D. G. *ACS Applied Materials & Interfaces*, 3, 2820-2829.
(3) Ista, L. K.; Dascier, D.; Ji, E.; Parthasarathy, A.; Corbitt, T. S.; Schanze, K. S.; Whitten, D. G. *ACS Applied Materials & Interfaces*, 3, 2932-2937.
(4) Ji, E.; Parthasarathy, A.; Corbitt, T. S.; Schanze, K. S.; Whitten, D. G. *Langmuir*, 27, 10763-10769.
(5) Jiang, H.; Taranekar, P.; Reynolds, J. R.; Schanze, K. S. *Angew. Chem., Int. Ed.* 2009, 48, 4300-4316.

(6) Arnt, L.; Nusslein, K.; Tew, G. N. *J. Polym. Sci., Part A: Polym. Chem.* 2004, 42, 3860-3864.
(7) Arnt, L.; Tew, G. N. *J. Am. Chem. Soc.* 2002, 124, 7664-7665.
(8) Arnt, L.; Tew, G. N. *Langmuir* 2003, 19, 2404-2408.
(9) Zhou, Z.; Corbitt, T. S.; Parthasarathy, A.; Tang, Y.; Ista, L. K.; Schanze, K. S.; Whitten, D. G. *J. Phys. Chem. Lett.* 2010, 1, 3207-3212.
(10) Tang, Y.; Corbitt, T. S.; Parthasarathy, A.; Zhou, Z.; Schanze, K. S.; Whitten, D. G. *Langmuir* 2011, 27, 4956-4962.
(11) Tang, Y.; Hill, E. H.; Zhou, Z.; Evans, D. G.; Schanze, K. S.; Whitten, D. G. *Langmuir* 2011, 27, 4945-4955.
(12) Tang, Y. L.; Corbitt, T. S.; Parthasarathy, A.; Zhou, Z. J.; Schanze, K. S.; Whitten, D. G. *Langmuir* 2011, 47, 4956-1962.
(13) Patel, D. G.; Feng, F.; Ohnishi, Y.-y.; Abboud, K. A.; Hirata, S.; Schanze, K. S.; Reynolds, J. R. *J. Am. Chem. Soc.*, 134, 2599-2612.
(14) *Handbook of Thiophene-Based Materials: Applications in Organic Electronics and Photonics*; Perepichka, I. F.; Perepichka, D. F., Eds.; John Wiley & Sons Ltd.: Chichester, 2009; Vol. 1 & 2.
(15) Beaujuge, P. M.; Amb, C. M.; Reynolds, J. R. *Acc. Chem. Res.* 2010, 43, 1396-1407.
(16) Fang, Z.; Eshbaugh, A. A.; Schanze, K. S. *J. Am. Chem. Soc.* 2011, 133, 3063-3069.
(17) Wang, Y. S.; Schanze, K. S. *Chem. Phys.* 1993, 176, 305-319.
(18) Farley, R. T., University of Florida, 2007.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:

1. A compound of formula (I)

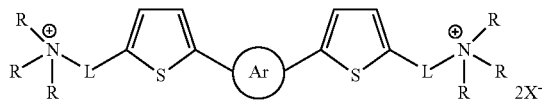

wherein
Ar is an aryl or heteroaryl ring system;
L is a linker comprising a 1-6 carbon chain, optionally comprising 1-2 heteroatom selected from the group consisting of O, NR, or S(O)q wherein q is 0, 1, or 2;
each R is independently selected from the group consisting of alkyl, cycloalkyl, two R together are alkylene or alkenylene such that the two R together with the nitrogen atom to which the two R are bound form a heterocyclyl, and three R together are trivalent alkylene or trivalent alkenylene such that the three R together with the nitrogen atom to which they are bound form a bicycloheterocyclyl such that the nitrogen atom to which the three R are bound is part of each of the two cycloheterocyclyl rings of the bicycloheterocyclyl ring;
optionally, wherein Ar is an electron donor ring system or an electron acceptor ring system; and,
each X is independently an anion.

2. The compound of claim 1 wherein Ar is thienyl.

3. The compound of claim 1 wherein X is chloride.

4. The compound of claim 1 wherein Ar is a 1,2,3-benzotriazolyl of formula

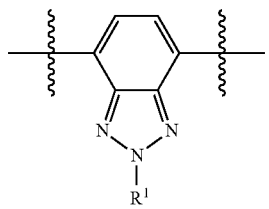

or a 2,1,3-benzothiadiazole of formula

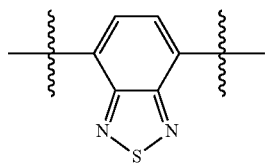

wherein $R^1$ is H or (C1-C6)alkyl, wherein a wavy line indicates a point of bonding.

5. The compound of claim 1, wherein each R is methyl.

6. The compound of claim 1, wherein each L is $(CH_2)_n$ wherein n=1, 2, 3, 4, 5, or 6.

7. The compound of claim 1, wherein the compound is any

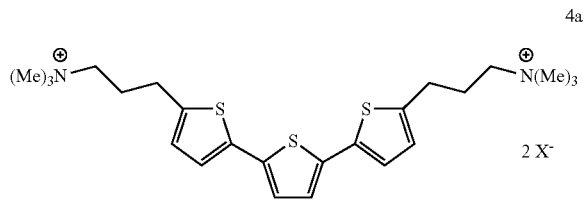

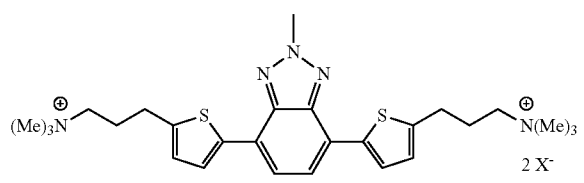

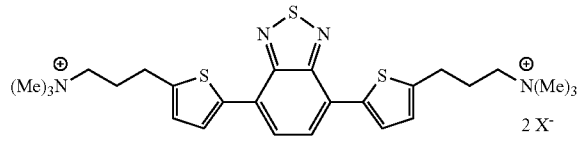

of wherein each Me signifies a methyl group, and X is a halide, a sulfonate, a phosphate, or a carboxylate anion.

8. A method of killing a microorganism or attenuating a population of the microorganism, comprising contacting the microorganism or the population thereof with an effective amount or concentration of a compound of claim 1, optionally under illumination.

9. The method of claim 8, wherein the microorganism or population thereof comprises bacteria.

10. The method of claim 9, wherein bacteria comprise *Staphylococcus aureus*.

11. A method of decontaminating a surface contaminated with a microorganism or a population thereof, comprising contacting the microorganism or the population thereof disposed on the contaminated surface with an effective amount or concentration of a compound of claim 1, optionally under illumination.

12. The method of claim 11, wherein the microorganism or population thereof comprises bacteria.

13. The method of claim 12, wherein bacteria comprise *Staphylococcus aureus*.

14. A method of decontaminating a fabric contaminated with a microorganism or a population thereof, comprising contacting the microorganism or the population thereof disposed on or within fibers of the contaminated fabric with an effective amount or concentration of a compound of claim 1, optionally under illumination.

15. The method of claim 14, wherein the microorganism or population thereof comprises bacteria.

16. The method of claim 15, wherein bacteria comprise *Staphylococcus aureus*.

17. A method of decontaminating a transparent liquid contaminated with a microorganism or a population thereof, comprising contacting the microorganism or the population thereof disposed within the transparent liquid with an effective amount or concentration of a compound of claim 1, optionally under illumination.

18. The method of claim 17, wherein the microorganism or population thereof comprises bacteria.

19. The method of claim 18, wherein bacteria comprise *Staphylococcus aureus*.

20. A kit for decontamination of a surface, a fabric, or a transparent liquid, comprising a composition including the compound of claim 1, optionally in a suitable solvent or medium; and, optionally, a source of illumination; optionally comprising additional biocidal materials; and optionally including instructions for use.

\* \* \* \* \*

UNITED STATES PATENT AND TRADEMARK OFFICE
CERTIFICATE OF CORRECTION

| | | |
|---|---|---|
| PATENT NO. | : 9,125,415 B2 | Page 1 of 1 |
| APPLICATION NO. | : 14/127465 | |
| DATED | : September 8, 2015 | |
| INVENTOR(S) | : Schanze et al. | |

It is certified that error appears in the above-identified patent and that said Letters Patent is hereby corrected as shown below:

On the title page, in item (75), in "Inventors", in column 1, line 3, delete "Gainsville," and insert --Gainesville,--, therefor On the title page, in item (75), in "Inventors", in column 1, line 6, delete "le" and insert --Le--, therefor On the title page, in item (75), in "Inventors", in column 1, line 8, delete "le" and insert --Le--, therefor On the title page, in item (73), in "Assignees", in column 1, line 1, delete "STC, UNM," and insert --STC.UNM,--, therefor On page 2, in column 2, item (56) References Cited under "Other Publications", line 12, delete "electronc" and insert --electron--, therefor In the Claims In column 18, line 36, in Claim 4, delete "(C1-C6)alkyl," and insert --$(C_1-C_6)$alkyl,--, therefor In column 18, line 41, in Claim 7, after "any", insert --of--, therefor In column 19, line 1, in Claim 7, before "wherein", delete "of", therefor Signed and Sealed this
Twenty-eighth Day of June, 2016

Michelle K. Lee
*Director of the United States Patent and Trademark Office*